United States Patent [19]

Krempl et al.

[11] Patent Number: 4,518,861
[45] Date of Patent: May 21, 1985

[54] METHOD FOR THE CONTINUOUS MEASUREMENT OF THE MASS OF AEROSOL PARTICLES IN GASEOUS SAMPLES AND A DEVICE FOR THE IMPLEMENTATION OF THE METHOD

[75] Inventors: Peter W. Krempl; Wolfgang Schindler, both of Graz; Leopold Faschingleitner, Mank, all of Austria

[73] Assignee: Hans List, Graz, Austria

[21] Appl. No.: 439,596

[22] Filed: Nov. 5, 1982

[30] Foreign Application Priority Data

Nov. 9, 1981 [AT] Austria ................................. 4814/81

[51] Int. Cl.$^3$ ............................................. G01J 1/00
[52] U.S. Cl. ..................................... 250/339; 250/343
[58] Field of Search ....................... 250/339, 341, 343; 356/437, 438, 439

[56] References Cited

U.S. PATENT DOCUMENTS 3,281,597 10/1966 Greenberg ......................... 250/343
4,229,653 10/1980 Uthe .................................... 250/339

Primary Examiner—Janice A. Howell
Attorney, Agent, or Firm—Watson, Cole, Grindle & Watson

[57] ABSTRACT

For a continuous measurement of the mass of absorbing particles in a gaseous sample, the sample is traversed by electromagnetic radiation of a wavelength greater than the mean radius of the particles. The difference in absorption for at least two frequencies is determined and appointed to the particle mass sought after.

16 Claims, 11 Drawing Figures

METHOD FOR THE CONTINUOUS MEASUREMENT OF THE MASS OF AEROSOL PARTICLES IN GASEOUS SAMPLES AND A DEVICE FOR THE IMPLEMENTATION OF THE METHOD

BACKGROUND OF THE INVENTION

The invention relates to a method and device for the continuous measurement of the mass of aerosol particles in gaseous samples, for example in the exhaust of internal combustion engines, in which the sample is traversed by electromagnetic radiation of a wavelength greater than the mean radius of the aerosol particles and in which the absorption caused is measured and is used as a measurement value corresponding to the total mass of aerosol particles.

DESCRIPTION OF THE PRIOR ART

Methods for the continuous measurement of the mass of aerosol particles in gaseous samples are known in which the sample which is loaded with the particles is traversed by a light beam and in which the absorption or scattering caused by the particles is measured. In one of the known methods the radiation wavelengths used are of the same order of magnitude as the radii of the particles, i.e. the measurement is taken in the so-called optical Mie range. In this range the absorption coefficient per mass and thus the overall absorption measured will greatly depend on the particle size, and for this reason the total mass of aerosol particles cannot be determined without determining at least the mean particle size at the same time. As regards the measurement of aerosol particles in the exhaust of internal combustion engines it is known, e.g., that the mean particle size will depend on the fuel used, or rather on its additives, and on the operational state of the engine. For this reason a measurement using this known method will only permit a rough estimate of the total mass of aerosol particles actually emitted.

In another one of the known methods radiation of a greater wavelength is employed, e.g., in the infrared range. With these wavelengths, the absorption coefficient per mass is independent of the particle size; the measurement is taken in the optical Rayleigh range, the employed wavelength being much greater than the mean radius of the aerosol particles, preferably at least twice as long. Since, however, the absorption cross-section of aerosol particles will decrease considerably with an increasing wavelength of the incident radiation, the accuracy obtained with the very small measurement signal will be diminished radically in this known method on account of external influences.

For this reason special measuring techniques have become known for differentiating between changes in the measured absorption due to actual variations in particle emission and changes due to fluctuations having their origin in the equipment, e.g., fluctuations in the intensity of the radiation source. One of these known arrangements is based on the use of spectrophonics, i.e., the transformation of the absorbed light energy into heat, which will produce sound pulses due to the expansion of the absorbing medium or its carrier gas, which are detected by a microphone. As opposed to the measurement by extinction, in which the difference in radiation intensity before and after the test chamber is determined and which requires a long-term stability of radiation sensors and precise subtraction techniques, spectrophonic or photoacoustic/spectroscopic techniques of measurement will directly yield a signal proportional to the light energy absorbed. The major disadvantage of this known method is the high sensitivity to external sound radiation, which will prevent its being employed in the vicinity of internal combustion engines. Above all, a direct measurement at the exhaust manifold will not be possible within reasonable limits of expense, since this is one of the noisiest parts of an internal combustion engine.

SUMMARY OF THE INVENTION

It is an object of the present invention to avoid the above drawbacks of the known methods and to improve on a method of the aforementioned type so as to yield in as simple a manner as possible a measurement value for the total mass of aerosol particles in gaseous samples which is independent of the mean particle size and largely insensitive to disturbances caused by external influences.

According to the present invention this is achieved by measuring absorption for at least two different frequencies, and by using as a measurement value corresponding to the total mass of particles the difference of the signals which have been received for the different frequencies and which are proportional to the respective absorption. A particular advantage is gained if the difference in absorption at the different frequencies is directly measured, as is suggested in one variant of the invention. As is known, the absorption cross-section of the aerosol particles and thus the total absorption caused by the particles will depend on the wavelength of the incident radiation; this kind of measurement will therefore yield a differential signal whose magnitude may be determined with great precision. By utilizing the variation of the absorption cross-section with frequency, it will be possible in a simple manner to separate fluctuations in the total mass of absorbing particles from equipment-generated fluctuations, as for instance fluctuations in the intensity of the radiation source, since a fluctuation in the total mass of absorbing particles will effect a change in the differential signal on account of the different cross-sections of absorption, whereas in the case of a fluctuation in the source intensity the differential signal of the measurement value will remain constant for the different frequencies. A detailed description of the measurement method by differential absorption, as covered by the present invention, will be given under "Description of the Drawing".

An enhanced version of the invention provides that a narrow-band radiation source be wobbled over a certain frequency range with a given period, and that, after the radiation has passed the sample, that part of the detected signal varying with the wobbling period be taken as the measurement value. Thus a narrow frequency band is filtered out and shifted between two limiting frequencies with an adjustable period, before the radiation has traversed the sample. That part of the detector signal to be determined by known methods, which varies with the wobbling period of the incident radiation, is further processed as measurement value, thereby permitting discrimination against very high background noise which may have a value 100–1000 times higher than the measurement value proper. The only important point to be observed is that the detector signal should remain constant during the wobbling of the measurement frequencies, if no aerosol particles are contained in the sample. In this context, another proposal of the invention is particularly advantageous which provides that the wobbling range of the narrow-band radiation source contain at least part of the resonance absorption band of the aerosol particles to be measured and that that part of the detector signal be used as a measurement signal which correlates with the shape of a reference signal corresponding to the absorption band. The characteristic shape of the absorption band will permit an even better suppression of background noise by means of state-of-the-art electronic correlators, which will further improve measurement accuracy.

According to another variant of the invention a narrow frequency band is selected between preselectable frequencies by means of a selector unit with a preset period, from a radiation source with an at least partially continuous spectrum, after the radiation has passed the sample, and the part of the radiation intensity varying with the given period behind the selector unit is used as measurement value. In this way the sample is traversed by radiation of different frequencies which is reduced to certain narrow-frequency bands by corresponding filters with a preset period only after the radiation has passed the sample, i.e., after absorption by the aerosol particles.

In another variant of the invention, a detector is exposed to the selected radiation frequencies in turn, with a given periodicity, the apparatus being set in such a way that the radiation intensities arriving at the detector when no aerosol particles are contained in the test volume, are adjusted the equal values for these frequencies. Thus a detector is provided which is fed the selected radiation frequencies one after the other. In this context the invention provides that a beam splitter be positioned in the radiation path behind the sample chamber, and that behind the above splitter selectively transparent filters be inserted into the partial beams for the frequencies selected, and that a selector unit be added which will open the passage to the detector for one partial beam at a time, with the given periodicity. As is proposed in a further variant, this selector unit may consist of a rotating disk which is placed in the radiation path in front of the detector and has openings for the partial beams opening a passage to the detector in turn. This is a simple and robust design which will guarantee that the frequencies are properly applied to the detector in turn if the openings for the partial beams are configured and positioned in suitable manner. Another variant of the invention will permit the selector unit to operate with polarizers of different direction in the partial beams and with a polarizer in front of the detector, which transmits the different polarization directions in turn, with the given periodicity. This design will eliminate the effects of manufacturing and assembly tolerances of the selector unit on the measurement signal, which results in a further increase in measurement accuracy.

In further enhancement of the above devices for the implementation of the measurement method according to the present invention provisions are made for a lock-in amplifier for the evaluation of the detector signals, which is connected to the detector and to a pulse generator attached to the selector unit, the pulse generator supplying clock signals with a preselected periodicity. This will permit in a simple manner to discriminate detector signals which do not vary with the given period, thereby contributing to the measurement accuracy as discussed above.

In another proposal of the invention the method is conceived such that, after having passed the sample, the radiation of each of the frequencies used for the absorption measurement is detected separately, and that the difference of the radiation intensities at the different frequencies is registered only. This proposal therefore implies a separate detector for each of the radiation frequencies used for the measurement method, the detectors preferably being connected such that only the difference of the radiation intensities after absorption is registered. In this context, a periodic modulation of the radiation intensity, as suggested in yet another variant of the invention, will be of great advantage, which again will provide the above-mentioned benefits concerning the discrimination of those parts of the detector signal which do not vary with the preselected frequency.

According to another proposal an absorber with a known absorption capacity may periodically be introduced into the radiation path for the purpose of calibration during the measurement process, i.e., preferably with a period being an integral multiple of the period of frequency change of the incident radiation. In this way the measurement set-up may be calibrated during the measurement process, thus permitting a continuous monitoring of the accuracy of the measurement results.

Another enhanced version of the invention provides that, in addition to radiation traversing the sample, which is attenuated by absorption, the radiation scattered by the sample is also measured, preferably in a solid angle greater than 10 degrees. Additionally taking into account the scattered radiation will contribute towards a closer characterization of the aerosol particles. Whereas the scattering intensity within a narrow angular range will provide no satisfactory answer as to the size of the individual particles, the scattered radiation yield over a larger angular range will correlate with the size or size distribution of the aerosol particles. If a minimum of two frequencies of the incident radiation are selected as described and if the scattering intensities are registered separately, additional information may be gained on the optical properties of the aerosol particles.

DESCRIPTION OF THE DRAWING

Following is a more detailed description of various embodiments of the invention, as illustrated by the enclosed diagrams.

DESCRIPTION OF THE PREFERRED EMBODIMENTS

Following is a short explanation of the principle upon which the method for the continuous measurement of the mass of aerosol particles in gaseous samples is based, as shown in FIGS. 1 through 7 of the present invention.

Figure 1:
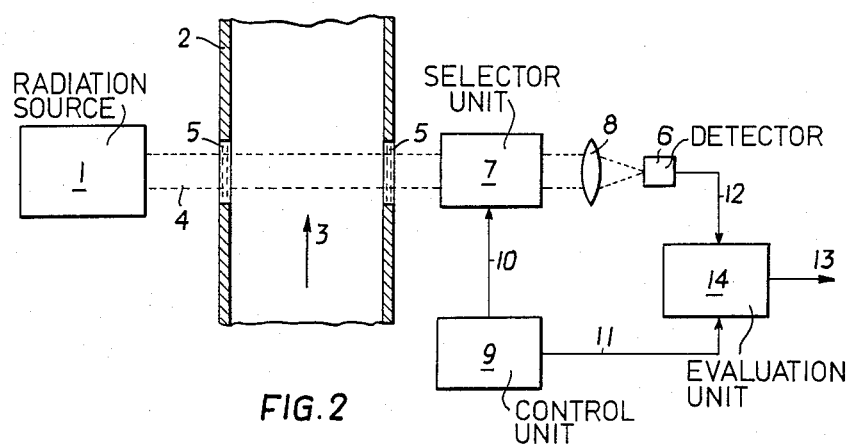
FIGS. 1, 2 each show a basic set-up according to the method of the present invention.

The set-up presented in FIG. 1 shows a radiation source 1 emitting electromagnetic radiation in the optical Rayleigh range, i.e., with wavelengths considerably longer than the mean radius of the aerosol particles, preferably at least twice as long, e.g., infrared radiation. In a test chamber 2 the gaseous sample to be measured is conveyed past two windows 5 (for instance in the direction of arrow 3) in the path 4 of the radiation from the source 1, which should have maximum transparency for the radiation used. The radiation leaving the test chamber whose attenuation due to absorption depends on the mass of aerosol particles contained in the sample, is registered by a detector 6, in front of which a selector unit 7 and a focusing lens 8 are located in the variant shown in FIG. 1. In addition, a control unit 9 is provided which is connected to the selector unit via a line 10 and to an evaluation unit 14 via a line 11. Via a line 12 the evaluation unit 14 is supplied with the measurement signal of the detector 6; the measurement value obtained may be further processed or displayed via an output line 13.

In this variant the radiation source 1 has an at least partially continuous spectrum; for this reason the sample in test chamber 2 is subject to radiation containing a multitude of frequencies. By means of the selector unit 7 controlled by the control unit 9, a narrow frequency band is selected from the spectrum of incident radiation, which is focused on the detector 6 by the focusing lens 8, where it will generate a signal in accordance with its intensity, which is fed to the evaluation unit 14 via line 12.

Figure 3:
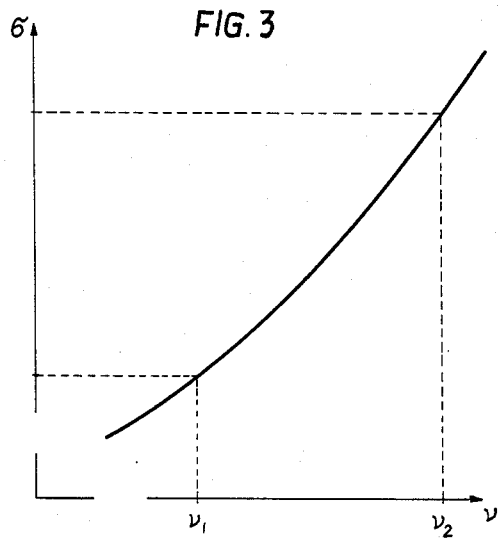
FIGS. 3, 4 are plots of the absorption cross-section of aerosol particles as functions of the radiation frequency.

In FIG. 3 the absorption cross-section $\sigma$ of aerosol particles is plotted along the ordinate and the frequency $\gamma$ of the incident radiation is plotted along the abscissa. As can be seen, the absorption by the aerosol particles contained in the sample varies with the radiation frequency. The measuring method of the present invention utilizes this dependency. In the set-up shown in FIG. 1 for example, the absorption by aerosol particles contained in the sample is measured for at least two frequencies; the difference of the signals obtained at the individual frequencies, which are proportional to the absorption, is used as a measurement value. This is a simple and effective way of increasing measurement accuracy, which is of importance since in the case of long-wave radiation in the Rayleigh range, the absorption cross-section of aerosol particles is very small already, which will result in a strong background noise in the measurement signal.

Figure 6:
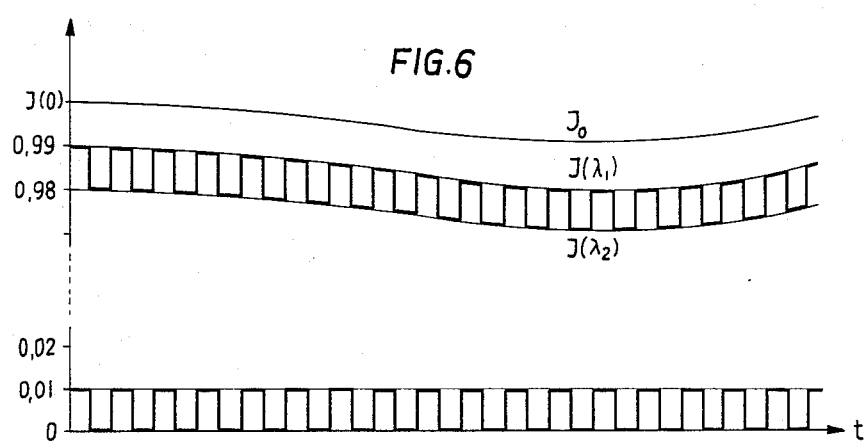
FIGS. 6, 7 show intensity/time diagrams explaining the advantage of the method proposed by the invention.
Figure 7:
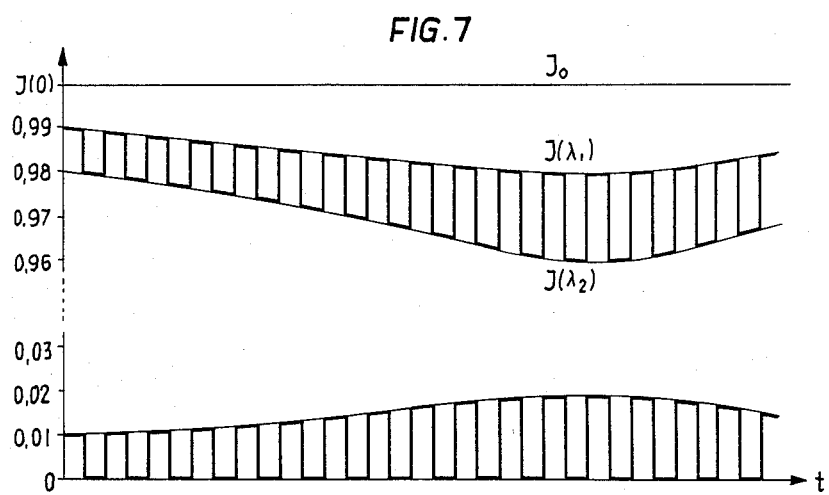

Using the set-up presented in FIG. 1, the intensity/time diagrams shown in FIGS. 6, 7 may be obtained by switching the selector unit 7 via the control unit 9 between two frequencies or wavelengths $\lambda_1$, $\lambda_2$, the clock-rate of this change of wavelengths being applied to the evaluation unit 14 via the line 11. The evaluation unit 14 may be configured as a lock-in amplifier using for measuring purposes only those parts of the detector signals coming in via line 12 which oscillate with the period given by the control unit. In FIGS. 6, 7 $I_o$ denotes the intensity of the radiation source without any attenuation caused by aerosol particle absorption, $I(\lambda_1)$ denotes the intensity registered by the detector at wavelength $\lambda_1$, $I(\lambda_2)$ the radiation intensity registered by the detector at wavelength $\lambda_2$. The lower parts of FIGS. 6, 7 show the measurement signal obtained at output 13 of the evaluation unit 14.

FIG. 6 is concerned with a case in which the radiation intensity of the radiation source 1 is not constant over time, i.e., it oscillates at a comparatively low frequency. On the assumption of constant aerosol particle density—as is represented in FIG. 6—both $I(\lambda_1)$ and $I(\lambda_2)$ will change in accordance with the change of $I_o$. Due to differencing, the measurement signal will remain constant, however.

In FIG. 7 the radiation intensity $I_o$ remains constant while the total mass of aerosol particles in the sample varies over time. This is reflected in corresponding variations of $I(\lambda_1)$ and $I(\lambda_2)$, which are synchronous but not identical, because of the frequency characteristic of the absorption cross-section shown in FIG. 3. In this case, the measurement signal will therefore be characterized by a change reflecting the changing mass of aerosol particles in the sample volume subject to the radiation.

In FIGS. 6, 7 the same time curve of $I(\lambda_1)$ was chosen in both cases, in order to demonstrate that the actual change in density of the aerosol particles (FIG. 7) may be separated from source fluctuations (FIG. 6) only by measuring at a minimum of two frequencies as proposed by the present invention.

Apart from switching the radiation registered by the detector between two preselected frequencies (cf. FIGS. 6, 7), the arrangement presented in FIG. 1 will permit wobbling of the selector unit 7 between two preselected frequencies with a preselected period, each time passing only a narrow frequency band, and to use the part of the detector signal oscillating with the preselected period for a measurement value.

Figure 2:
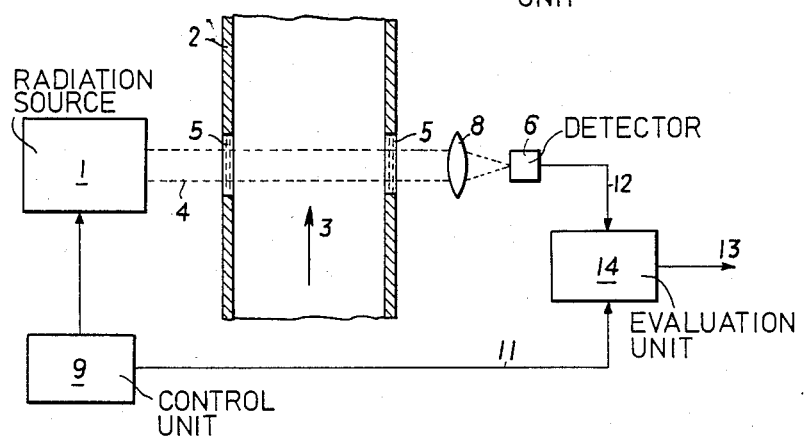

The arrangement presented in FIG. 2 is much the same as that in FIG. 1, the only difference being that the control unit 9 does not act upon a selector unit situated in the radiation path behind the test chamber 2, but acts directly upon the radiation source 1. If a suitable narrow-band radiation source has been selected, it may be wobbled over a given frequency range by the control unit 9 with a preset wobbling period. For the remaining steps of measurement and evaluation the same applies as discussed before.

Figure 4:
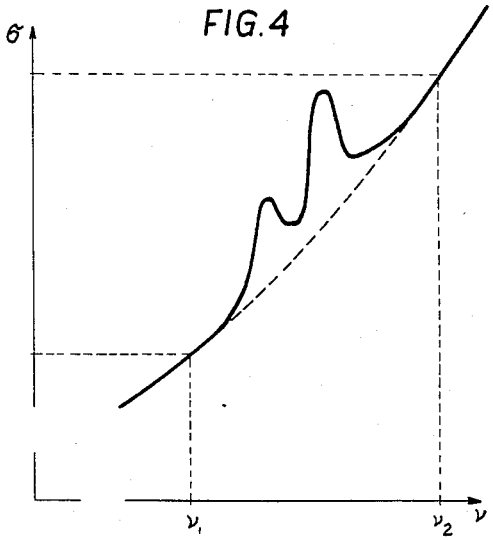

FIG. 4 shows the absorption cross-section of aerosol particles as a function of frequency in the case that the frequency range shown contains resonance frequencies of these particles. The simple switchover between two frequencies and the evaluation along the principles already discussed under FIGS. 6, 7 are made possible in a simple manner by choosing the two measurement frequencies $\gamma_1$ and $\gamma_2$ outside of the resonance range.

Figure 5:
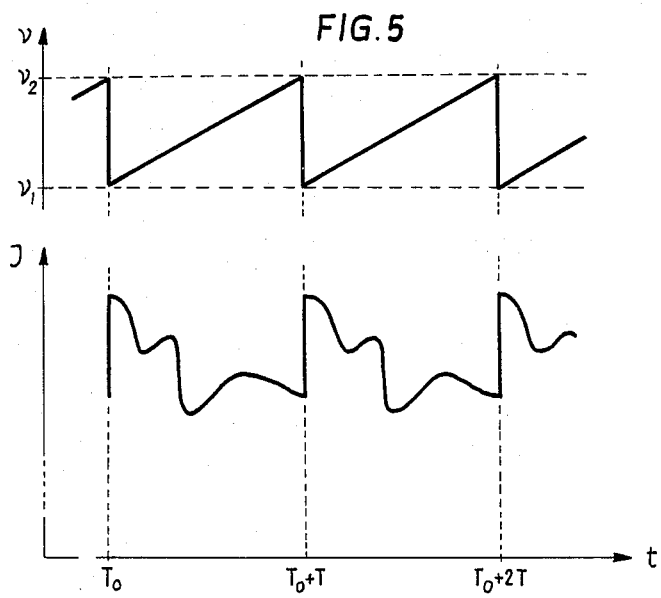
FIG. 5 shows a characteristic frequency curve over time (above), and the corresponding intensity/time diagram if the frequencies are wobbled over a range including resonances of the aerosol particles (below)

As is shown in FIG. 5, the special characteristic of the frequency dependence of the absorption cross-section in the resonance range may also be utilized intentionally for increasing the measurement accuracy. As is seen in the upper part of FIG. 5, the radiation registered by the detector is varied over time in a saw-tooth pattern between two frequencies $\gamma_1$ and $\gamma_2$, between which may be found resonances of the aerosol particles (but not of the carrier gas). In the lower part of FIG. 5 the radiation intensity I which is registered by the detector in this way, is represented as a function of time. Departing from an initial time $T_o$, the intensity curve determined by the resonance characteristics of the aerosol particle absorption, repeats itself with period T. The use of a so-called electronic correlator which is supplied with the characteristic shape of the frequency dependence of the absorption cross-section in the resonance range for a reference signal, permits filtering out that part of the signal registered by the detector whose time curve correlates with that of the above reference signal, which will further increase measurement accuracy.

Figure 8:
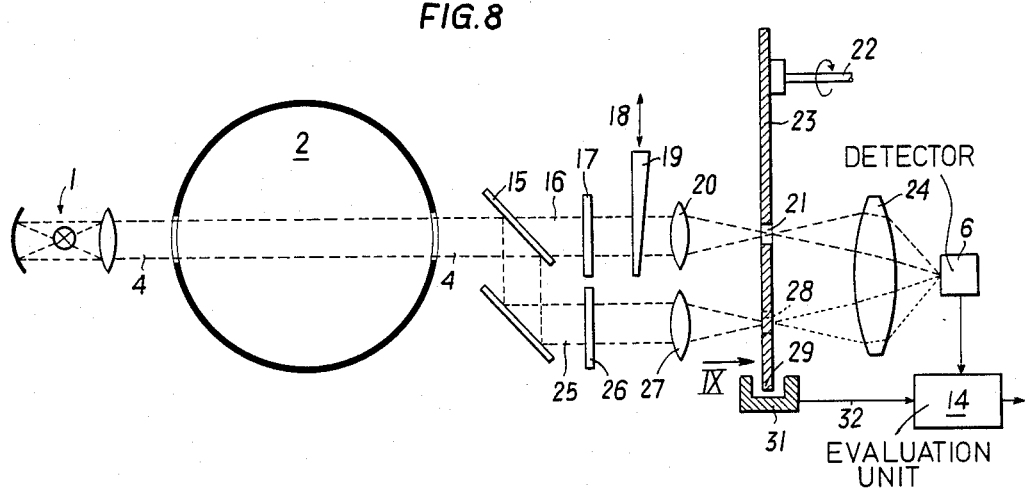
FIG. 8 is an example of a device for implementation of the method proposed by the invention.
Figure 9:
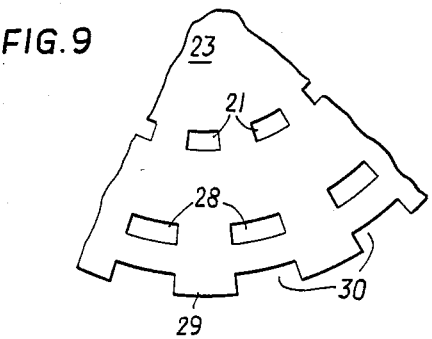
FIG. 9 shows an enlarged detail from FIG. 8, as seen in the direction of arrow IX in FIG. 8, FIGS. 10, 11 show further variants of measuring devices according to the invention.

In the device for the implementation of the method described by the present invention whose set-up is outlined in FIG. 8, a beam splitter 15 is placed in the radiation path 4 behind the test chamber 2, which is a semi-transparent mirror in this case. The undeflected partial beam 16 will arrive at a focusing lens 20 after having passed through a filter 17 of selective transparency and through an attenuating wedge 19 which may be shifted in the direction indicated by arrow 18. This lens 20 will focus the partial beam 16 on another focusing lens 24 and subsequently on the detector 6 through an opening 21 in a disk 23 rotating around an axis 22. The lower partial beam 25 will also arrive at a focusing lens 27, after having passed another selective filter 26 which is transparent at a frequency other than the one of filter 17 in the partial beam 16, and at the detector 6 via an opening 28 in the disk 23 and the focusing lens 24. It should be noted that the two partial beams 16, 25 may arrive at the focusing lens 24, or rather at the detector 6, through the corresponding opening 21, 28 only one at a time; the other partial beam is shut off by those parts of disk 23 which are not transparent. The openings 21, 28 are placed in such a way that the partial beams passing them will neither overlap in time nor be divided by any noticeable dark phases.

The entire set-up may be adjusted by means of the attenuating wedge 19 such that the detector 6 will register the same intensity for both partial beams if the sample contains no aerosol particles.

The rotatable disk 23 serving as a selector unit for the partial beams arriving at the detector, has regularly spaced notches 30 around its circumference 29, which generate clock signals corresponding to the given periodicity of the frequency change by means of a pulse generator 31, e.g., of the type of a light barrier. Via a line 32 these signals in turn are fed to an evaluation unit 14 which may be configured as a lock-in amplifier, for example.

As regards the execution and evaluation of measurements by means of this device, please refer to the description under FIGS. 1 through 7.

Figure 10:
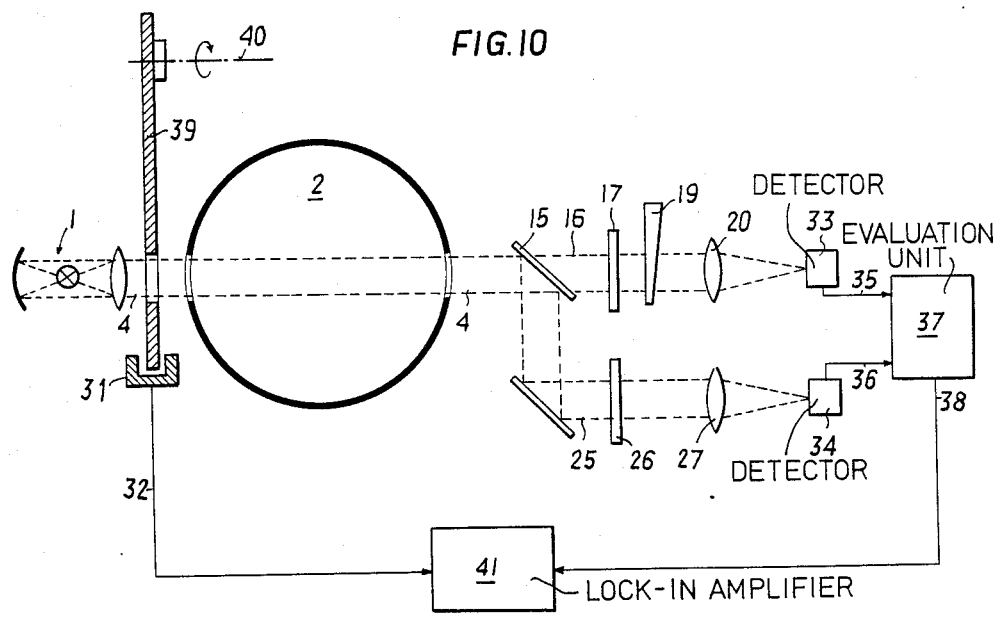

The device shown in FIG. 10 differs from that in FIG. 8 by the use of two separate detectors 33, 34 for registering the intensities of partial beams 16, 25. Via lines 35, 36 the output signals of the detectors 33, 34 are fed into an evaluation unit 37 whose output 38 represents the difference of the two detector signals. The attenuating wedge 19 in the upper partial beam 16 again will permit adjustment of the relation between the intensities of the two partial beams such that the value at output 38 of the evaluation unit 37 is zero when no aerosol particles are present in the test chamber 2 or, more specifically, in the radiation path 4.

In this variant a chopper disk 39 is placed in the radiation path 4 in front of the test chamber 2, which rotates around an axis 40 and modulates with a given periodicity the radiation emitted by the source 1. Once again, a pulse generator 31 will generate a clock signal which is fed into a lock-in amplifier 41 as a reference signal via a line 32, the amplifier being connected to the output 38 of the evaluation unit 37 by a line 42. This set-up again will permit to obtain test results of a satisfactory accuracy in the manner described, even for small absorption cross-sections of the aerosol particles to be measured.

Figure 11:
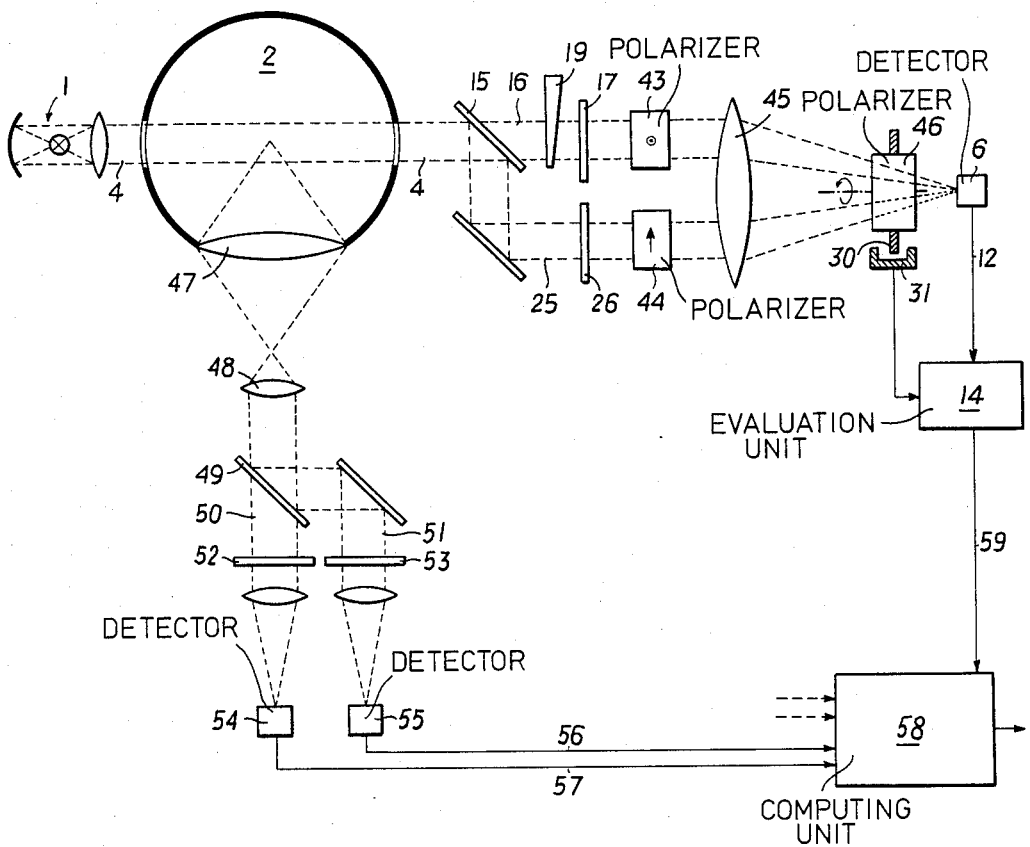

In the device shown in FIG. 11 the radiation emitted by the radiation source 1 again is split in the above-described manner into two partial beams 16, 25 after having passed the test chamber 2, from which beams narrow frequency bands will be filtered out by the selective filters 17, 26. The evaluation unit consists of the polarizers 43, 44 and of a rotatable polarizer 46 located in the path of the two partial beams behind the focusing lens 45. As the polarizers 43, 44 are placed in the partial beams 16, 25, respectively, having different directions of polarization, the rotatable polarizer 46 will pass a certain part of the partial beams 16, 25 only. Due to the geometry of the polarization process this set-up ensures, provided that the intensities of the partial beams entering the polarizers 43, 44 are identical, that the intensity registered by the detector 6 will remain constant over time as long as there are no aerosol particles in the test chamber 2. Compared to the set-up presented in FIG. 8, this arrangement has the advantage that a slight error in the adjustment of the polarizers 43, 44 and of polarizer 46 will affect the intensity registered by the detector 6 far less than in the case of the evaluation unit shown in FIG. 8.

The circumference of the rotatable polarizer 46 again has periodicity notches 30 for generating clock signals for the evaluation unit 14 via a pulse generator 31. Again, the evaluation unit 14 is configured as a lock-in amplifier e.g., and is connected to the detector 6 by a line 12.

In addition to the radiation attenuated by absorption, the radiation scattered by the sample in a direction essentially normal to the passing radiation, is also measured in the variant shown in FIG. 11. For this purpose, the casing of the test chamber 2 contains a focusing lens 47 which focuses the scattered radiation coming from a particular solid angle, and transmits it by way of another focusing lens 48 to a semi-transparent mirror 49 which will split it into two partial beams 50, 51. Once again, two filters of selective transparency 52, 53, having different pass bands, are inserted into the radiation path, which will permit determination of the intensity of the scattered radiation for different frequencies by means of detectors 54, 55. Via lines 56, 57 the output signals of the detectors 54, 55 are fed to a computing unit, e.g., a microprocessor, which is also supplied with the output signal of the evaluation unit 14 via a line 59. In the computing unit 58 the incoming measurement signals are combined by suitable arithmetic operations in such a way that the additional information obtained by the scattering arrangement may be displayed besides the total mass, i.e., mean particle size and/or chemical composition of the aerosol particles. Computing these additional quantities will only be possible after an exact determination of the total particle mass.

Splitting the radiation used for the absorption measurement into two partial beams with different frequencies, as shown in FIGS. 8, 10, 11, might of course also be performed before the beams enter the test chamber. This would in no way affect the practicability of the method proposed by the present invention, but would not be advantageous as there would be no simple way to ensure that both partial beams traverse the same measurement volume and thus the same mass of aerosol particles, which might lead to measurement errors.

Other practicable ways of splitting the beams include, e.g., the use of a semi-transparent mirror which is made transparent for a certain frequency only, and of a reflecting mirror for the second partial beam which is also made reflective for a certain frequency only, so that no selective filters will be needed in the partial beams. The proper adjustment of the relative radiation intensities for the different measurement frequencies, which in the variants shown is achieved by the use of movable attenuating wedges, might also be obtained by changing the radiation temperature of the radiation source, for example.

Besides, all variants shown will permit the periodical insertion into the radiation path of an absorber of a known absorption capacity, which will be used for calibration purposes during the measurement process, and whose insertion period might be selected as an integral multiple of the period of the frequency change of the incident radiation. This absorber might consist of a rotating disk of a transparent material, divided into an even number of sectors—every other sector being charged with a given amount of aerosol particles—which will result in the same attenuation of radiation as is given in the sample volume for a given charge of aerosol particles. After inserting the calibration absorber the detector signal will consist of the measurement signal plus the calibration signal, with both the period and amplitude of the latter being known. If the sensitivity of the two detectors were shifted in a set-up according to FIG. 10, e.g., the calibration signal would no longer correspond to the value set at calibration time. This deviation could be sensed in the evaluation unit and the correct sensitivity value could be restored by means of a control circuit.

We claim:

1. A method for the continuous measurement of the mass of aerosol particles in gaseous samples, wherein a sample being traversed by electromagnetic radiation of a wavelength greater than the mean radius of said aerosol particles, and the absorption caused being measured for at least two different frequencies, and wherein the difference of the signals which have been received for the different frequencies and which are proportional to the respective absorption is used as a measurement value corresponding to the total mass of said aerosol particles.

2. A method as in claim 1, wherein the difference in absorption at said different frequencies is directly measured.

3. A method as in claim 2, wherein a narrow-band radiation source is wobbled over a certain frequency range with a given period, and wherein that part of the signal detected after the radiation has passed the sample, which varies with the wobbling period, is taken as the measurement value.

4. A method as in claim 3, wherein the wobbling range of said narrow-band radiation source contains at least part of the resonance absorption band of the aerosol particles to be measured, and wherein that part of the detector signal is used as a measurement signal which correlates with the shape of a reference signal corresponding to said absorption band.

5. A method as in claim 1 or 2, wherein a narrow frequency band is selected between preselectable frequencies by means of a selector unit with a preset period, from the radiation of a radiation source with an at least partially continuous spectrum, after said radiation has passed said sample, and wherein the part of the radiation intensity varying with the given period behind said selector unit is used as measurement value.

6. A method as in claim 1 or 2, wherein a detector is exposed to the selected radiation frequencies in turn, with a given periodicity, and the radiation intensities arriving at said detector when no aerosol particles are contained in said sample, are adjusted to equal values for these frequencies.

7. A method as in claim 1, wherein said radiation of each of said frequencies used for the absorption measurement is detected separately after having passed said sample, and wherein preferably the difference of the radiation intensities at the different frequencies is registered only.

8. A method as in claim 7, wherein said radiation intensity is periodically modulated.

9. A method as in claim 1, wherein an absorber with a known absorption capacity is periodically introduced into the radiation path for the purpose of calibration during the measurement process.

10. A method as in claim 9, wherein said absorber is introduced into said radiation path with a period being an integral multiple of the period of frequency change of the incident radiation.

11. A method as in claim 1, wherein in addition to said radiation traversing said sample, which is attenuated by absorption, the radiation scattered by said sample is also measured in a solid angle greater than 10 degrees.

12. A device for the continuous measurement of the mass of aerosol particles in a gaseous sample which includes a sample chamber for containing said gaseous sample; means for directing a beam of electromagnetic radiation through said sample chamber, said electromagnetic radiation having at least two different wavelengths which are longer than the expected means radius of the aerosol particles in the gaseous sample in said sample chamber; a beam splitter for splitting said beam into partial beams after said beam has passed through said sample chamber; means for inserting selectively transparent filters into the partial beams for selected frequencies; a detector; and a selector unit for enabling said detector to be exposed to said partial beams at a given periodicity.

13. A device as in claim 12, wherein said selector unit comprises a rotating disk which is placed in the radiation path in front of said detector and has openings for the partial beams opening a passage to said detector in turn.

14. A device as in claim 12, wherein said selector unit is provided with polarizers of different directions in said partial beams, and with an additional polarizer in front of said detector, which transmits the different polarization directions in turn, with the given periodicity.

15. A device as in claims 12, 13 or 14, wherein a lock-in amplifier is provided for the evaluation of the detector signals, which is connected to said detector and to a pulse generator attached to said selector unit, said pulse generator supplying clock signals with a preselected periodicity.

16. A method for the continuous measurement of the mass of aerosol particles in a gaseous sample, the aerosol particles having an expected mean radius, said method comprising the steps of
   (a) passing a beam of electromagnetic radiation through said gaseous sample, said electromagnetic radiation having at least two different wavelengths which are longer than said expected mean radius, (b) measuring the absorption by said mass of aerosol particles in said gaseous sample at at least two of said different wavelengths to obtain two measurement signals, and
(c) determining the difference between said two measurement signals so as to provide a measurement value which corresponds to the total mass of said aerosol particles in said gaseous sample.

* * * * *